US00PP16373P2

(12) United States Plant Patent
Kerley et al.

(10) Patent No.: US PP16,373 P2
(45) Date of Patent: Mar. 21, 2006

(54) ***PRIMULA* PLANT NAMED 'KERBELBUT'**

(50) Latin Name: *Primula acaulis*
Varietal Denomination: Kerbelbut

(76) Inventors: David W. Kerley, Bethany, 49 Station Road, Over, Cambridge, CB4 5NJ (GB); Priscilla G. Kerley, Bethany, 49 Station Road, Over, Cambridge, CB4 5NJ (GB)

( * ) Notice: Subject to any disclaimer, the term of this patent is extended or adjusted under 35 U.S.C. 154(b) by 51 days.

(21) Appl. No.: 11/046,000

(22) Filed: Jan. 28, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Primula* plant named 'Kerbelbut', characterized by its upright, compact and uniform plant habit; large, double, fragrant and bright yellow-colored flowers that are held upright on strong and erect peduncles; large sepals that "frame" the flowers; freely flowering habit; and tolerance to low temperatures.

2 Drawing Sheets

Botanical designation: *Primula acaulis.*
Cultivar denomination: 'Kerbelbut'.

BACKGROUND OF THE INVENTION

The present Invention relates to a new and distinct cultivar of *Primula* plant, botanically known as *Primula acaulis,* and hereinafter referred to by the cultivar name Kerbelbut.

The new *Primula* is a product of a planned breeding program conducted by the Inventor in Over, Cambridge, United Kingdom. The objective of the breeding program was to create new compact pot-type *Primula* cultivars with numerous double flowers with short peduncles and attractive leaf and flower coloration.

The new *Primula* originated from a cross-pollination made by the Inventors in Over, Cambridge, United Kingdom of two unnamed proprietary *Primula acaulis* seedling selections, not patented, in March, 2001. The new *Primula* was discovered and selected by the Inventor as a flowering plant within the progeny of the stated cross-pollination in a controlled environment in Over, Cambridge, United Kingdom in February, 2002.

Asexual reproduction of the new cultivar by tissue culture since the summer of 2002 in Enniscorthy, Ireland, has shown that the unique features of this new *Primula* are stable and reproduced true to type in successive generations.

SUMMARY OF THE INVENTION

Plants of the cultivar Kerbelbut have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Kerbelbut'. These characteristics in combination distinguish 'Kerbelbut' as a new and distinct cultivar:

1. Upright, compact and uniform plant habit.
2. Large, double, fragrant and bright yellow-colored flowers that are held upright on strong and erect peduncles.

3. Large sepals that "frame" the flowers.
4. Freely flowering habit.
5. Tolerant to low temperatures.

Plants of the new *Primula* differ from plants of the parent selections in the following characteristics:

1. Plants of the new *Primula* are more compact than plants of the parent selections.
2. Plants of the new *Primula* have double flowers whereas plants of the parent selections have single flowers.
3. Plants of the *Primula* are sterile whereas plants of the parent selections are fertile.

Plants of the new *Primula* can be compared to plants of the *Primula acaulis* cultivar Val Horncastle, not patented. In side-by-side comparisons conducted in Over, Cambridge, United Kingdom, plants of the new *Primula* differed from plants of the cultivar Val Horncastle in the following characteristics:

1. Plants of the new *Primula* were more compact than plants of the cultivar Val Horncastle.
2. Plants of the new *Primula* had smaller leaves than plants of the cultivar Val Horncastle.
3. Plants of the new *Primula* had larger flowers than plants of the cultivar Val Horncastle.
4. Plants of the new *Primula* had bright yellow-colored flowers whereas plants of the cultivar Val Horncastle had pale yellow-colored flowers.
5. Plants of the new *Primula* had larger sepals than plants of the cultivar Val Horncastle.
6. Plants of the new *Primula* had strong upright peduncles whereas plants of the cultivar Val Horncastle had weak arching peduncles.

Plants of the new *Primula* can be compared to plants of the *Primula acaulis* cultivar Sunshine Susie, not patented. In side-by-side comparisons conducted in Over, Cambridge, United Kingdom, plants of the new *Primula* differed from plants of the cultivar Sunshine Susie in the following characteristics:

1. Plants of the new *Primula* were more vigorous and stronger than plants of the cultivar Sunshine Susie.
2. Plants of the new *Primula* had larger flowers than plants of the cultivar Sunshine Susie.
3. Plants of the new *Primula* had larger sepals than plants of the cultivar Sunshine Susie.
4. Plants of the new *Primula* flowered earlier than plants of the cultivar Sunshine Susie.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Primula*.

The photograph on the first sheet comprises a side perspective view of a typical flowering plant of 'Kerbelbut' grown in a 11-cm container.

The photograph on the second sheet is a close-up view of a typical flower of 'Kerbelbut'.

DETAILED BOTANICAL DESCRIPTION

The aforementioned photographs, following observations and measurements describe plants grown in Over, Cambridge, United Kingdom, in a glass-covered greenhouse and under commercial production practices during the spring. Plants were about four to five months old when the photographs and description were taken. During the production of the plants, day temperatures ranged from 20 to 28° C. and night temperatures ranged from 15 to 20° C. In the following description, color references are made to The Royal Horticultural Society Colour Chart, 1995 Edition, except where general terms of ordinary dictionary significance are used.

Botanical classification: *Primula acaulis* cultivar Kerbelbut.

Parentage:

*Female, or seed, parent.*—Unnamed proprietary *Primula acaulis* seedling selection, not patented.

*Male, or pollen, parent.*—Unnamed proprietary *Primula acaulis* seedling selection, not patented.

Propagation:

*Type.*—By tissue culture.

*Time to initiate roots.*—About four weeks at 20° C.

*Time to produce a rooted young plant.*—About five weeks at 20° C.

*Root description.*—Fibrous; white in color.

*Rooting habit.*—Freely branching.

Plant description:

*Plant form/habit.*—Upright, compact and uniform plant habit; inverted triangle. Vigorous growth habit. Leaves basal.

*Plant height.*—About 10 to 16 cm.

*Plant width (spread).*—About 25 cm.

*Foliage description.*—Arrangement: Basal, simple. Length: About 8 to 12 cm. Width: About 2.8 to 5.5 cm. Shape: Oblanceolate. Apex: Obtuse. Base: Acute. Margin: Slightly crenate; irregular; undulate. Texture, upper surface: Slightly rugose; smooth. Texture, lower surface: Prominent venation; pubescent. Venation pattern: Pinnate. Color: Developing leaves, upper surface: 138A to 143B. Developing leaves, lower surface: 146A to 146B. Fully expanded leaves, upper surface: 137A to 144A. Fully expanded leaves, lower surface: 137B to 144A. Venation, upper surface: 144A. Venation, lower surface: 147C. Petiole length: About 1.5 to 2.2 cm. Petiole diameter: About 6 to 10 mm. Petiole texture, upper and lower surfaces: Smooth, glabrous. Petiole color, upper surface: 59B to 59C. Petiole color, lower surface: 59C.

Flower description:

*Flower type/habit.*—Single, rounded double flowers; flowers face upright and outward. Freely flowering habit with about 13 flower buds and flowers per plant.

*Fragrance.*—Moderately fragrant; typical of species.

*Natural flowering season.*—Recurrent flowering during the spring in the United Kingdom. Flowers persistent.

*Flower buds.*—Height: About 8 to 11 mm. Diameter: About 5 to 8 mm. Shape: Ovoid. Color: 145A to 145D.

*Flower diameter.*—About 1.8 to 2.8 cm.

*Flower depth.*—About 1.2 to 1.9 cm.

*Petals.*—Quantity per flower: About 20 to 26 in several concentric whorls. Length (including tube): About 7 to 13 mm. Width: About 9 to 16 mm. Shape: Obcordate. Apex: Emarginate. Margin: Mostly entire. Texture, upper and lower surfaces; Smooth, glabrous; satiny. Color: Developing petals, upper surface: 3A to 3B. Developing petals, lower surface: 3C to 3D. Fully expanded petals, upper surface: 9A to 9C; color becoming closer to 14A to 2B with development. Fully expanded petals, lower surface: 2A to 2B.

*Sepals.*—Quantity per flower: Typically four or five in a single whorl, fused at the base; sepals are large and "frame" the flower. Length: About 1.7 to 3 cm. Width: About 1 to 2.5 cm. Shape: Rounded to oblong. Apex: Obtuse. Texture, upper and lower surfaces: Smooth, glabrous; rugose. Color, upper surface: 137A to 137B. Color, lower surface: 138A to 138B.

*Peduncles.*—Length: About 4.5 to 8.5 cm. Diameter: About 2 to 3 mm. Orientation: Mostly erect. Strength: Strong. Texture: Pubescent. Color: 60C to 60D.

*Reproductive organs.*—Development of reproductive organs has not been observed.

Disease/pest resistance: Plants of the new *Primula* have not been noted to be resistant to pathogens and pests common to *Primula*.

Temperature tolerance: Plants of the new *Primula* have been observed to have tolerate temperatures from about −5 to 28° C.

It is claimed:

1. A new and distinct cultivar of *Primula* plant named 'Kerbelbut', as illustrated and described.

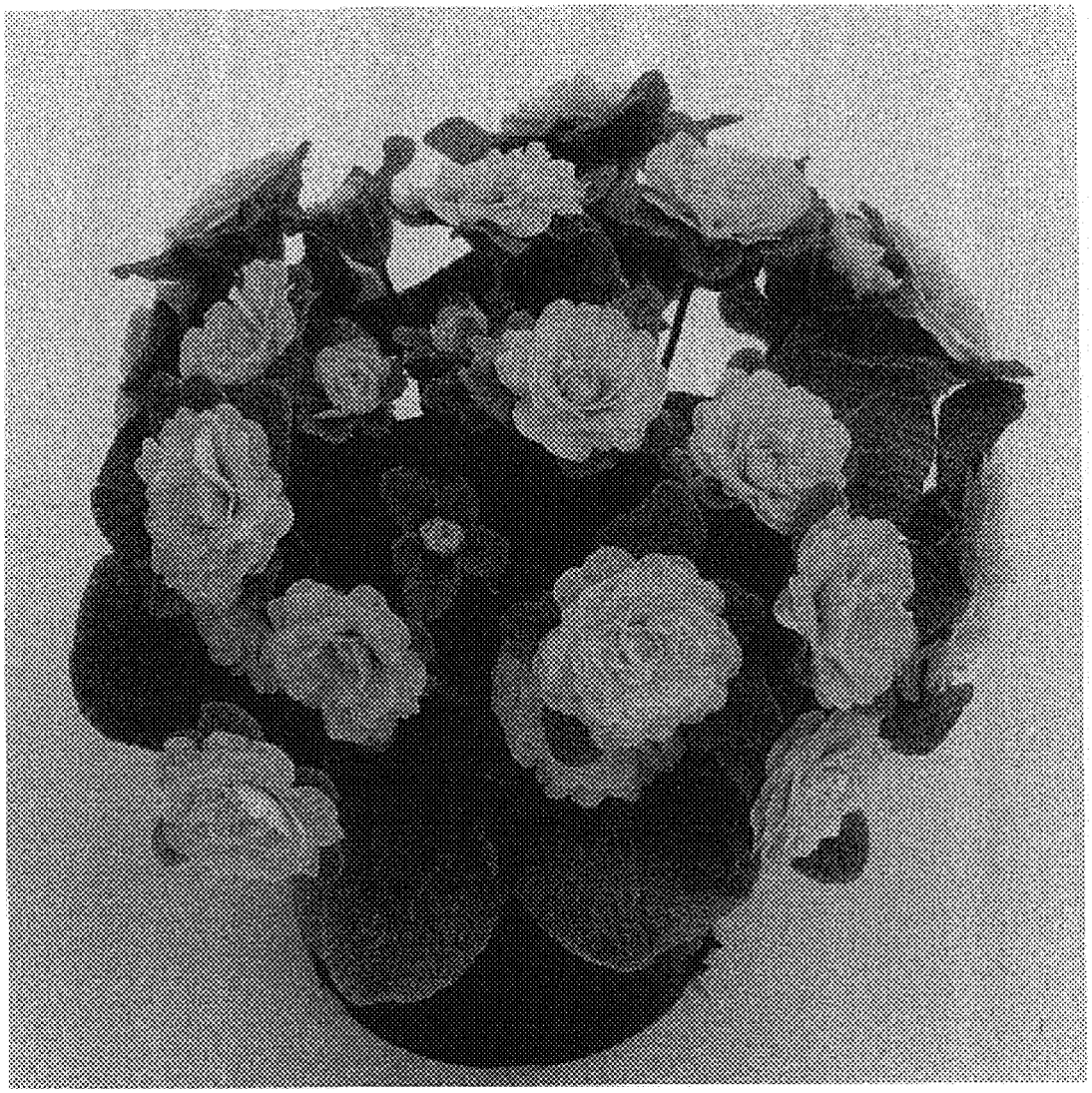

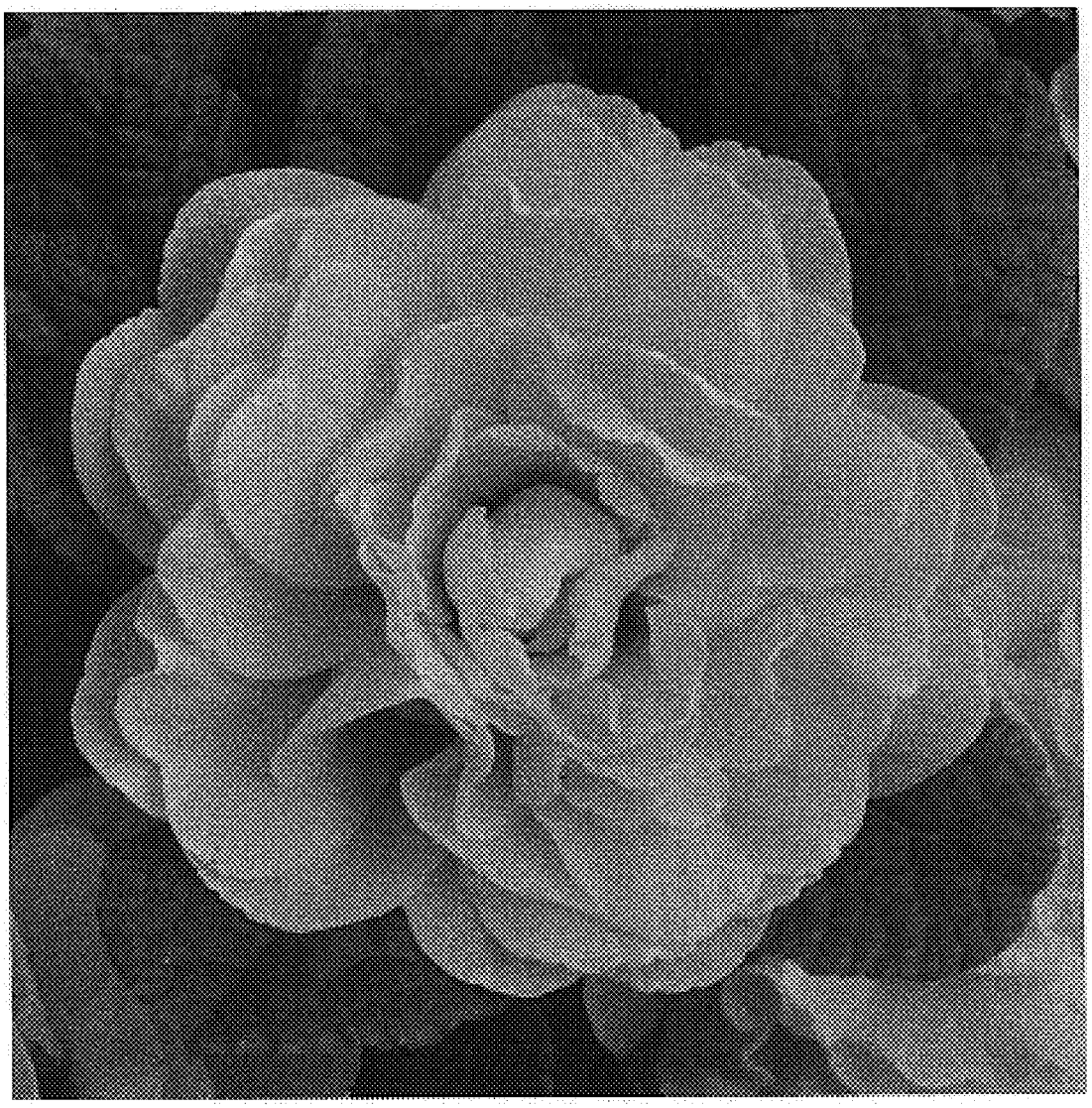

* * * * *